United States Patent [19]

Sakamoto et al.

[11] 4,389,408

[45] Jun. 21, 1983

[54] NOVEL AMPICILLIN ESTERS AND PRODUCTION THEREOF

[75] Inventors: Fumio Sakamoto, Osaka; Shoji Ikeda, Ibaraki; Goro Tsukamoto, Toyonaka; Isamu Utsumi, Kyoto, all of Japan

[73] Assignee: Kanebo Ltd., Tokyo, Japan

[21] Appl. No.: 327,735

[22] Filed: Dec. 4, 1981

Related U.S. Application Data

[63] Continuation-in-part of Ser. No. 257,562, Apr. 27, 1981, abandoned.

[30] Foreign Application Priority Data

Apr. 30, 1980 [JP]  Japan .................................. 55-58510
May 22, 1980 [JP]  Japan .................................. 55-68444

[51] Int. Cl.³ .................... A61K 31/43; C07D 499/32; C07D 499/42
[52] U.S. Cl. ................................ 424/271; 260/239.1; 260/245.2 R
[58] Field of Search ..................... 260/239.1, 245.2 R; 424/271

[56] References Cited

U.S. PATENT DOCUMENTS 3,951,954  4/1976  Murakami et al. ............. 260/239.1

FOREIGN PATENT DOCUMENTS 55-33444  8/1980  Japan .
1215812  12/1970  United Kingdom .
1363506   8/1974  United Kingdom .
1364672   8/1974  United Kingdom .

Primary Examiner—Natalie Trousof
Assistant Examiner—Vera C. Clarke
Attorney, Agent, or Firm—Wenderoth, Lind & Ponack

[57] ABSTRACT

A novel Ampicillin ester of the general formula

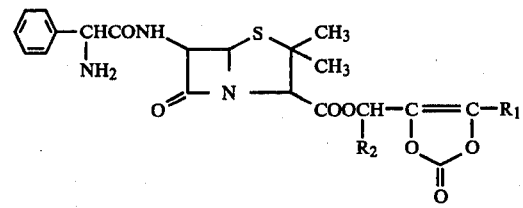

wherein $R_1$ represents a hydrogen atom, a methyl group or an aryl group, and $R_2$ represents a hydrogen atom or may be taken together with $R_1$ to form a divalent carbon chain residue, or its acid addition salt.

The novel Ampicillin ester or its acid addition salt is prepared by (1) reacting a corresponding 6-N-acylamino penicillanic acid (II) or its salt with a compound of the formula

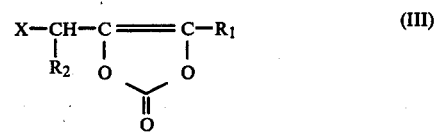

wherein $R_1$ and $R_2$ are as defined above, and X is a halogen atom, or reacting a compound of the formula

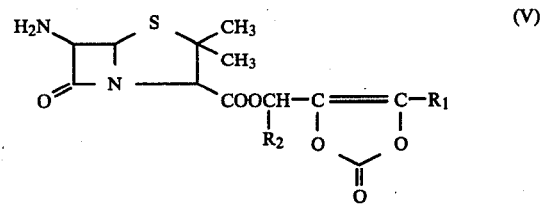

wherein $R_1$ and $R_2$ are as defined above, or its acid addition salt with a corresponding carboxylic acid (VI) or its reactive derivative, (2) thereafter, if required, when the resulting compound has the protected amino group or the group convertible to an amino group, deprotecting the protected amino group or converting said convertible group to an amino group, and (3) if further required, converting the product to an acid addition salt.

The present invention provides also an antibacterial agent comprising the novel Ampicillin ester and a method for the treatment of infectious disease.

9 Claims, No Drawings

Ampicillin ester of the invention (i.e.,(2-oxo-1,3-dioxolen-4-yl)methyl group) is shown by a formula below in comparison with those of the known prodrugs.

| | Ester group |
|---|---|
| Ampicillin pivaloyloxy methyl ester | $-CH_2O-\overset{O}{\underset{\|}{C}}-C(CH_3)_3$ |
| Ampicillin phthalidyl ester | 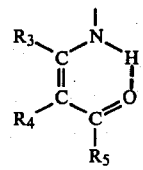 |
| Ampicillin ester of the invention | $-CH-C=\!=\!=C-R_1$ with $R_2$, $O$, $O$, and $C=O$ |

It is clear therefore that the ester group of the Ampicillin ester of the invention quite differs from those of the known Ampicillin esters. It is surprising that the Ampicillin esters of the present invention have the aforesaid excellent properties as pharmaceuticals over these known Ampicillin esters.

According to one process of the invention, the Ampicillin ester or its acid addition salt of the invention can be produced by reacting a compound of the general formula

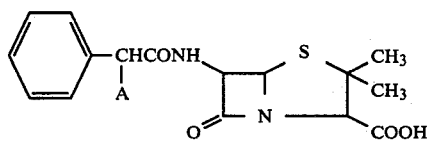 (II)

wherein A represents a protected amino group or a group convertible to an amino group, or its salt at the carboxyl group with a compound of the general formula

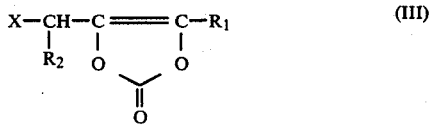 (III)

wherein $R_1$ and $R_2$ are as defined above, and X represents a halogen atom, and if required, when the resulting compound has the protected amino group or the group convertible to an amino group, eliminating the protecting group from the protected amino group or converting said convertible group to an amino group, and if further required, converting the product to its acid addition salt.

In the above general formula (II), A represents a protected amino group or a group convertible to an amino group. The protected amino group may preferably be an amino group in the form of a salt with a mineral acid, an amino group in the form of a Schiff base, an enamine group, a benzyloxycarbonylamino group, etc. More specifically, preferred protected amino groups are amino groups in the form of salts with mineral acids such as hydrochloric acid and hydrobromic acid, amino groups in the form of Schiff base such as a substituted or unsubstituted benzylideneamino group, and enamine groups of the following formula $$\begin{array}{c} R_3 \\ \diagdown \\ C \\ \| \\ R_4 - C \\ \diagdown \\ R_5 \end{array} \begin{array}{c} N-H \\ \| \\ O \end{array}$$

wherein $R_3$, $R_4$ and $R_5$ are identical or different and represent an alkyl, aralkyl or aryl group, provided that $R_4$ may further represent a hydrogen atom and $R_5$ may further represent an alkoxy, aralkoxy or aryloxy group.

An example of the group convertible to an amino group is an azido group.

These protective amino groups and convertible groups are well known in the field of chemistry of synthetic penicillins.

A compound corresponding to general formula (II) in which A is a free amino group is a compound well known as Ampicillin and readily available commercially.

Accordingly, the compound of general formula (II) can be produced by converting the free amino group of Ampicillin to the group A (in this case, the group A is desirably a protected amino group).

The compound of general formula (II) can also be produced by reacting 6-aminopenicillanic acid or its salt at the carboxyl group with a carboxylic acid of the formula

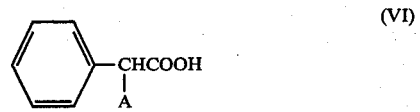 (VI)

wherein A is as defined hereinabove, or its reactive derivative at the carboxyl group. Such a process for producing the compound of formula (II) is described, for example, in U.S. Pat. No. 3,120,514.

The compound of general formula (III) is a novel compound. In formula (III), $R_1$ and $R_2$ are as defined above with regard to formula (I), and X represents a halogen, preferably chlorine, bromine and iodine.

Examples of the compound of formula (III) are
4-chloromethyl-1,3-dioxolen-2-one,
4-bromomethyl-1,3-dioxolen-2-one,
4-chloromethyl-5-phenyl-1,3-dioxolen-2-one,
4-bromomethyl-5-phenyl-1,3-dioxolen-2-one,
4-chloromethyl-5-methyl-1,3-dioxolen-2-one,
4-bromomethyl-5-methyl-1,3-dioxolen-2-one,
4-iodomethyl-5-methyl-1,3-dioxolen-2-one,
3-chloro-1,2-carbonyldioxycyclohexene,
3-bromo-1,2-carbonyldioxycyclohexene,
3-chloro-1,2-carbonyldioxycyclooctene, and
3-bromo-1,2-carbonyldioxycyclooctene.

These compounds can be produced by reacting compounds corresponding to formula (III) in which X is a hydrogen atom with halogenating agents, for example allylic halogenating agents such as chlorine, bromine, N-bromosuccinimide and N-chlorosuccinimide. The compounds of general formula (III) and their production are described in the specification of a patent application filed by the same applicants as U.S. application Ser. No. 257,564, filed Apr. 27, 1981.

The aforesaid process for production in accordance with this invention is carried out by reacting the compound of general formula (II) with the compound of general formula (III).

In the reaction, the compound of general formula (III) is used preferably in an amount of 1 mole or slightly more than 1 mole per mole of the compound of general formula (II). The reaction is performed usually in a solvent system consisting substantially of an aprotic inert organic solvent. In other words, the presence of a substantial amount of water or a protonic solvent such as alcohols in the reaction system is undesirable because it induces hydrolysis of the compound of general formula (III). Examples of preferred aprotic inert organic solvents are dimethyl formamide, dimethyl sulfoxide, acetone, ethyl acetate and mixtures thereof. Desirably, the reaction is performed in the presence of a base. If, however, a salt at the carboxyl group of the compound of general formula (II) is used, the reaction proceeds favorably in the absence of a base. Preferred bases to be present in the reaction system or used for formation of the salt include trialkylamines such as triethylamine, and metal hydrogen carbonates such as potassium hydrogen carbonate and sodium hydrogen carbonate. The reaction temperature is usually not more than 50° C.

The above reaction of the compound of formula (II) or its salt with the compound of general formula (III) usually gives a compound of the general formula

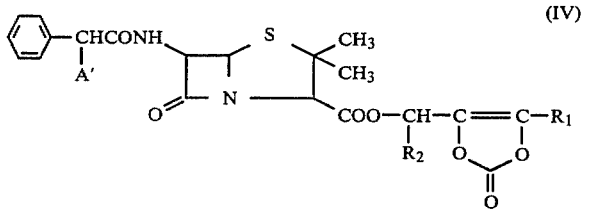

(IV)

wherein $R_1$ and $R_2$ are as defined above and A' represents a protected amino group, a group convertible to an amino group, or an amino group. When the compound of general formula (II) is in the form of a salt with a mineral acid, and the amount of the base present in the reaction system is in molar excess, the resulting compound may sometimes be a compound of general formula (IV) in which A' is a free amino group.

When the resulting product (IV) has the protected amino group or the group convertible to an amino group, the protected amino group is deprotected, or the convertible group is converted to an amino group.

The reaction conditions in such a step are well known in the field of synthetic penicillins. For example, when the protective amino group is in the form of a Schiff base such as a substituted or unsubstituted benzylideneamino group, the resulting reaction mixture containing the compound (IV) is adjusted to a pH of 1–4 in a mixed solvent of water and a water-miscible solvent such as acetonitrile, acetone and dioxane in the presence of an acid such as mineral acids and acetic acid. As a result, the protected amino group is easily hydrolyzed to an amino group at room temperature or at a lower temperature.

When the protected amino group is in the form of an enamine group, the reaction mixture is dissolved in a water-soluble solvent, the solution is adjusted with an acid to a pH of B 1.5–3.5, and stirred at room temperature or at a lower temperature for several minutes to about an hour. As a result, the protected amino group can be deprotected.

When the group A' is a benzyloxycarbonyl-protected amino group, or an azido group, the reaction product is treated in hydrogen gas in the presence of a hydrogenolysis catalyst such as palladium.

Thus, the Ampicillin ester of general formula (I) or its acid addition salt is formed. The acid addition salt is prepared by reacting the Ampicillin ester (having a free amino group) of general formula (I) with an acid, for example, an inorganic acid such as hydrochloric acid, hydrobromic acid, hydriodic acid and sulfuric acid or an organic acid such as citric acid or tartaric acid.

According to preferred embodiments of the process of the invention, there are provided a process for producing the Ampicillin ester of general formula (I) or its acid addition salt, which comprises reacting a compound of general formula (II) in which A is a Schiff base group or an enamine group with the compound of general formula (III), and converting the Shciff base group or the enamine group of the product to an amino group, and thereafter if required, converting the product to its acid addition salt; and a process for producing a mineral acid salt (e.g., hydrochloride) of the Ampicillin ester of general formula (I) which comprises reacting a compound of general formula (II) in which A is an amino group in the form of a mineral acid such as hydrochloride, with the compound of general formula (III).

According to another process provided by the invention, the Ampicillin ester of general formula (I) or its acid addition salt can be produced by reacting a compound of general formula

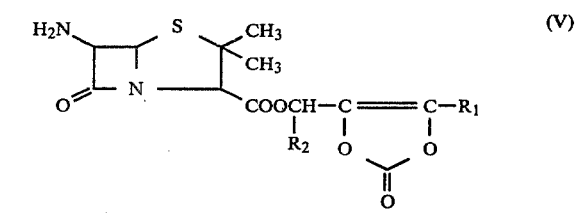

(V)

wherein $R_1$ and $R_2$ are as defined above, or its acid addition salt, with a carboxylic acid of the general formula

(VI)

wherein A is as defined above, or its reactive derivative at the carboxyl group; thereafter, if required, when the resulting compound has the protected amino group or the group convertible to an amino group, eliminating the protective group from the protected amino group, or converting said convertible group to an amino group, and if further required, converting the product to an acid addition salt thereof.

The precursor of general formula (V) and its acid addition salt are novel compounds and form part of the present invention.

In general formula (V), $R_1$ and $R_2$ are the same as defined above.

Examples of the compound of general formula (V) are (2-oxo-1,3-dioxolen-4-yl)methyl 6-aminopenicillanate,
(5-methyl-2-oxo-1,3-dioxolen-4-yl)methyl 6-aminopenicillanate,
(2-oxo-5-phenyl-1,3-dioxolen-4-yl)methyl 6-aminopenicillanate,
(2,3-carbonyldioxy-2-cyclohexen-1-yl) 6-aminopenicillanate,
(2,3-carbonyldioxy-2-cycloocten-1-yl) 6-aminopenicillanate, and
acid addition salts of these esters.

The compound of general formula (V) can be produced by reacting 6-aminopenicillanic acid or its salt at the carboxyl group with the compound of general formula (III); or by reacting 6-protected aminopenicillanic acid or its salt at the carboxyl group with the compound of general formula (III) and then converting the protected amine group of the reaction product to an amino group.

The former can be performed preferably by reacting 6-aminopenicillanic acid or its salt at the carboxyl group with an equimolar amount, or a molar excess, of the compound of general formula (III) in an inert organic solvent such as tetrahydrofuran, dioxane or acetone in the optional presence of a base (when 6-aminopenicillanic acid is used, the presence of a base is preferred) at a temperature of from about 0° C. to room temperature.

The latter can be performed preferably by reacting 6-protected aminopenicillanic acid such as 6-aminopenicillanic acid having the amino group at the 6-position protected with an acyl group or trityl group, or 6-aminopenicillanic acid having the amino group at the 6-position protected as a Schiff base, or its salt at the carboxyl group, for example 6-phenylacetylaminopenicillanic acid (benzylpenicillin), with the compound of general formula (III) under the same conditions as in the first-mentioned process, thereafter reacting the resulting 6-protected aminopenicillanic acid ester with phosphorus pentachloride and a lower alcohol such as methanol at the temperature of dry ice-acetone in the presence of a basic compound such as N-methylmorpholin, quinoline and triethylamine, and thereafter causing water to act on the resulting imino ether to hydrolyze it.

According to the process of this invention, the compound of general formula (V) or its acid addition salt is first reacted with the carboxylic acid of general formula (VI) or its reactive derivative.

The acid addition salt of the compound of general formula (V) may be a mineral acid salt or an organic acid salt, for example such a mineral acid salt as a hydrochloride or hydrobromide, or such an organic acid salt as a para-toluenesulfonate.

Acid halides, acid anhydrides and mixed acid anhydrides are preferably used as the reactive derivative of the carboxylic acid of general formula (VI).

The reaction of the compound of general formula (V) or its acid addition salt with the carboxylic acid of general formula (VI) is carried out in the presence of a dehydrocondensing agent such as dicyclohexyl carbodiimide (DCC) or a mixture of DCC and 1-hydroxybenzotriazole, preferably in a solvent consisting substantially of an aprotic inert organic solvent such as dimethyl formamide, dimethyl sulfoxide, methylene chloride, dioxane and tetrahydrofuran at a temperature of not more than 50° C.

The reaction of the compound of general formula (V) or its acid addition salt with the reactive derivative of the carboxylic acid of general formula (VI) is carried out preferably in a solvent consisting substantially of an aprotic inert organic solvent such as dimethyl formamide, dimethyl sulfoxide, methylene chloride, dioxane, tetrahydrofuran and acetone at a temperature of not more than 50° C. When an acid addition salt of the compound expressed by general formula (V) is used, the reaction is preferably carried out in the presence of a base such as triethylamine.

The reactive derivative of the carboxylic acid of general formula (VI) used in the above reaction is preferably an acid halide such as an acid chloride when the group A in general formula (VI) is a protected amino group in the form of a salt with a mineral acid. The acid halide of the compound of general formula (VI) having such a group A can be conveniently produced by treating the compound of general formula (VI) having such a group A with a halogenating agent such as thionyl chloride, phosgene or phosphorus pentachloride because such group A is stable to acids.

The reactive derivative of the compound of general formula (VI) in which the group A is a protected amino group in the form of a Schiff base or an enamine group is preferably an acid anhydride or mixed acid anhydride. This reactive derivative can be produced conveniently by treating a salt, such as a trialkylamine salt, of the carboxylic acid of general formula (VI) in which the group A is such a protected amino group, with, for example, an alkyl haloformate such as ethyl chloroformate and isobutyl chloroformate.

The reaction between the compound of general formula (V) or its acid addition salt and the carboxylic acid of general formula (VI) or its reactive derivative gives the compound of general formula (IV). When the compound of formula (IV) has a protected amino group or a group convertible to an amino group, the protecting group is removed from the protected amino group, or the convertible group is converted to an amino group and if desired, the product is converted to its acid addition salt. Thus, the Ampicillin ester of general formula (I) or its acid addition salt is formed.

According to preferred embodiments of the above process, there are provided a process for producing the Ampicillin ester of general formula (I) or its acid addition salt which comprises reacting a compound of general formula (VI) in which A is a Schiff base group or an enamine group with the compound of general formula (V), thereafter converting the Schiff base group or the enamine group (A) of the resulting compound to an amino group and if required, converting the product into its acid addition salt; and a process for producing an acid addition salt, such as a hydrochloride, of the Ampicillin ester of general formula (I) which comprises reacting a compound of general formula (VI) in which A is in the form of an acid addition salt such as a hydrochloride with the compound of general formula (V).

After the reaction, the Ampicillin of general formula (I) or its acid addition salt can be isolated and purified in a customary manner.

The Ampicillin ester of general formula (I) or its pharmaceutically acceptable acid addition salt is converted back to Ampicillin in vivo when administered to an animal. Accordingly, this invention also provides an antibacterial agent comprising the Ampicillin ester of general formula (I) or its pharmaceutically acceptable acid addition salt as an active ingredient.

The antibacterial agent of this invention may consist only of the Ampicillin ester of general formula (I) or its pharmaceutically acceptable acid addition salt, or a mixture of it with a pharmaceutically acceptable carrier.

The pharmaceutically acceptable carrier may be those carriers which can be used in formulating Ampicillin. Examples are starch, lactose, hydroxypropyl cellulose, crystalline cellulose, magnesium stearate, and calcium stearate.

The antibacterial agent of the invention is administered orally, for example. It may be in a unit dosage form for oral administration, such as tablet (sugar-coated tablets), capsules, granules and powder.

The antibacterial agent of this invention is administered to man and other animals in a dose of 1 to 50 mg/kg body weight/day calculated as the Ampicillin ester (I) or its pharmaceutically acceptable salt.

The following Examples illustrate the present invention more specifically.

EXAMPLE 1

(1) Production of 4-bromomethyl-5-phenyl-1,3-dioxolen-2-one

In 150 ml of carbon tetrachloride was dissolved 2.4 g of 4-methyl-5-phenyl-1,3-dioxolen-2-one (synthesized by the method described in *Liebichs Annalen der Chemie*, Vol. 764, pages 116–124, 1972). N-bromosuccinimide (2.9 g) and a catalytic amount of α,α'-azobisisobutyronitrile were added to the solution, and the mixture was heated under reflux for 90 minutes. The reaction mixture was concentrated to one half of its volume, and the insoluble material was separated by filtration. The filtrate was concentrated, and the residue was recrystallized from a mixture of benzene and cyclohexane to give 2.3 g (yield 66%) of colorless needles having a melting point of 90.5° to 91.5° C. This product had the following properties.

Elemental analysis, molecular formula $C_{10}H_7BrO_3$: Calculated (%): C, 47.09; H, 2.77; Br, 31.33; Found (%): C, 47.22; H, 2.64; Br, 31.29.

IR (KBr): near 1825 cm$^{-1}$ ($\nu_{c=o}$).

NMR (CCl$_4$, δ(ppm)): 4.35 (—CH$_2$Br, s), 7.40 (benzene ring, s).

From these data, the product was identified as the title compound.

(2) Production of Ampicillin (2-oxo-5-phenyl-1,3-dioxolen-4-yl)methyl ester hydrochloride Ampicillin trihydrate (500 mg) was dispersed in 6 ml of dimethyl formamide, and 125 mg of potassium hydrogen carbonate was added. The mixture was cooled to 0° C. and stirred. Benzaldehyde (0.25 ml) was added, and the mixture was stirred at 0° C. for 2.5 hours. Then, 125 mg of potassium hydrogen carbonate and 320 mg of 4-bromomethyl-5-phenyl-1,3-dioxolen-2-one were added, and the mixture was further stirred at 0° C. for 3 hours.

After the reaction, the reaction mixture was poured into ice water and extracted with ethyl acetate. The extract was washed three times with ice water. The ethyl acetate layer was concentrated under reduced pressure to form a syrup. The syrup was dissolved in 4 ml of acetonitrile, and the pH of the solution was adjusted to 2.0 with dilute hydrochloric acid. The solution was then stirred at 0° C. for 30 minutes.

Water (10 ml) was added, and the mixture was concentrated under reduced pressure to distill off acetonitrile. The aqueous layer was repeatedly washed with ethyl acetate, and saturated with sodium chloride. The separated oily substance was extracted with 50 ml of methylene chloride, washed with a saturated aqueous solution of sodium chloride and dried over anhydrous sodium sulfate. The dried organic layer was concentrated until the amount of methylene chloride decreased to one half. Isopropyl alcohol (30 ml) was added, and the mixture was again concentrated under reduced pressure to give a colorless solid. The solid was collected by filtration, and washed successively with isopropyl alcohol and ether to give 320 mg (yield 46.4%) of Ampicillin (2-oxo-5-phenyl-1,3-dioxolen-4-yl)methyl ester hydrochloride as a colorless amorphous solid.

Melting point: 140° C. (decomp.).

Elemental analysis, molecular formula $C_{26}H_{25}N_3O_7S \cdot HCl \cdot 2H_2O$: Calculated (%): C, 52.39; H, 5.07; N, 7.05; S, 5.38; Found (%): C, 52.17; H, 4.83; N, 7.31; S, 5.64.

IR (KBr): 1830 cm$^{-1}$ (cyclic carbonate), 1785 cm$^{-1}$ (β-lactam), 1760 cm$^{-1}$ (ester), 1690 cm$^{-1}$ (amide).

NMR (DMSO-d$_6$, δ(ppm)): 1.32 and 1.45 (6H, methyl at the 2-position, s), 4.44 (1H, proton at the 3-position, s), 5.12 (1H, benzyl proton, s), 5.31

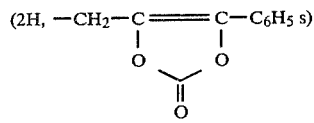

(2H, —CH$_2$—C=C—C$_6$H$_5$ s)

5.4–5.6 (2H, protons at the 5- and 6-positions, m), 7.3–7.6 (1OH, protons on the benzene ring, m), 8.8 (3H, —NH$_3^\oplus$), 9.3 (1H, —CONH—, d).

The resulting Ampicillin ester hydrochloride was incubated in 40% mouse blood in pH 7.4 phosphate buffer at 37° C. for 10 minutes, and then subjected to bioautography. It was found to be completely converted to Ampicillin.

EXAMPLE 2

(1) Production of 4-bromomethyl-5-methyl-1,3-dioxolen-2-one

In 150 ml of carbon tetrachloride was dissolved 3.42 g of 4,5-dimethyl-1,3-dioxolen-2-one (synthesized by the method described in *Tetrahedron Letters*, 1972 pages 1701–1704). N-bromosuccinimide (5.34 g) and a catalytic amount of α,α'-azobisisobutyronitrile were added to the solution, and the mixture was heated under reflux for 15 minutes. The reaction mixture was concentrated to one half of its volume, and the insoluble material was removed by filtration. The filtrate was concentrated, and the syrupy residue was distilled under reduced pressure to give 4.2 g (yield 73%) of a colorless liquid having a boiling point of 115°–120° C./5 mm. The product had the following properties.

Elemental analysis, molecular formula $C_5H_5BrO_3$: Calculated (%): C, 31.12; H, 2.61; Br, 41.40; Found (%): C, 31.30; H, 2.49; Br, 41.31.

IR (neat): near 1825 cm$^{-1}$ ($\nu_{c=o}$).

NMR (CCl$_4$, δ(ppm)): 2.10 (—CH$_3$, s), 4.10 (—CH$_2$Br, s).

From these data, the product was identified as the title compound.

(2) Production of Ampicillin (5-methyl-2-oxo-1,3-dioxolen-4-yl)methyl ester hydrochloride Ampicillin trihydrate (500 mg) was dispersed in 6 ml of dimethyl formamide, and 125 mg of potassium bicarbonate was added. The mixture was cooled to 0° C., and 0.25 ml of benzaldehyde was added. The mixture was stirred at 0° C. for 2.5 hours. Then, 125 mg of potassium bicarbonate and 250 mg of 4-bromomethyl-5-methyl-1,3-dioxolen-2-one were added, and the mixture was stirred at 0° C. for 3 hours. After the reaction, the reaction mixture was poured into ice water. The precipitated solid was extracted with 30 ml of ethyl acetate. The organic layer was washed with 20 ml of water three times, and dried over anhydrous magnesium sulfate. The ethyl acetate was distilled off under reduced pressure to give a yellow syrup. The resulting syrupy residue was dissolved in 4 ml of acetonitrile and the solution was adjusted to pH 2.0 with dilute hydrochloric acid. The solution was then stirred at 0° C. for 30 minutes. Water (10 ml) was added, and the acetonitrile was distilled off under reduced pressure. The aqueous layer was washed repeatedly with ethyl acetate, and then saturated with sodium chloride. The separated oily substance was extracted with 50 ml of methylene chloride, and washed with a saturated aqueous solution of sodium chloride. The methylene chloride layer was dried over anhydrous sodium sulfate, filtered and concentrated under reduced pressure to one half of its volume. To the solution isopropyl alcohol (30 ml) was added, and the mixture was again concentrated under reduced pressure to give a colorless amorphous solid.

The solid was collected by filtration and washed with isopropyl alcohol and ether to give 312 mg (yield 50.6%) of Ampicillin (5-methyl-2-oxo-1,3-dioxolen-4-yl)methyl ester hydrochloride as a colorless amorphous solid. The product had the following properties.

Appearance: Colorless amorphous solid.
Melting point: 145° C. (decomp.).
Elemental analysis, molecular formula $C_{21}H_{23}N_3O_7S\cdot HCl\cdot H_2O$: Calculated (%): C, 48.88; H, 5.08; N, 8.14; S, 6.21; Found (%): C, 48.51; H, 5.15; N, 8.02; S, 6.44.
IR (KBr): 1825 cm$^{-1}$ (cyclic carbonate), 1785 cm$^{-1}$ ($\beta$-lactam), 1750 cm$^{-1}$ (ester), 1690 cm$^{-1}$ (amide).
NMR (DMSO-$d_6$, $\delta$(ppm)): 1.33 and 1.48 (6H, methyl at the 2-position, s), 2.19

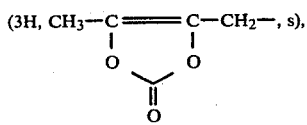

(3H, CH$_3$—C=C—CH$_2$—, s), 4.43 (1H, proton at the 3-position, s), 5.11

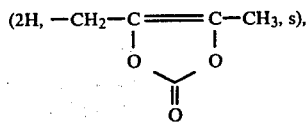

(2H, —CH$_2$—C=C—CH$_3$, s), 5.16 (1H, benzyl proton, s), 5.43–5.65 (2H, protons at the 5- and 6-positions, m), 7.3–7.6 (5H, protons on the benzene ring, m). 8.95 (3H, —NH$_3^\oplus$), 9.4 (1H, CONH—, d).

The resulting Ampicillin ester hydrochloride was incubated in 40% mouse blood in pH 7.4 phosphate buffer at 37° C. for 10 minutes, and then subjected to bioautography. It was found to be completely converted to Ampicillin.

EXAMPLE 3

(1) Production of 3-bromo-1,2-carbonyldioxycyclohexene

In 80 ml of carbon tetrachloride was dissolved 2.15 g of 1,2-carbonyldioxycyclohexene (synthesized by the method described in *Tetrahedron Letters*, 1972, pages 1701–1704). N-bromosuccinimide (2.3 g) and a catalytic amount of $\alpha,\alpha'$-azobisisobutyronitrile were added to the solution, and the mixture was heated under reflux for 20 minutes. The reaction mixture was cooled, and filtered. The filtrate was concentrated at a low temperature to give 3.2 g of a pale brown liquid as a residue. The product showed the following properties.

IR (neat): near 1825 cm$^{-1}$ ($\nu_{c=o}$).
NMR (CDCl$_3$, $\delta$(ppm)): 5.0 (=C—CH—Br, m), 1.3–3.0 (cyclic proton, m).

From these data, the product was identified as the title compound.

(2) Production of Ampicillin (2,3-carbonyldioxy-2-cyclohexenyl)-ester hydrochloride By the same method as shown in Example 1, (2), 256 mg of Ampicillin (2,3-carbonyldioxy-2-cyclohexenyl)ester hydrochloride was obtained as a colorless amorphous solid from 2 g of Ampicillin trihydrate and 1 g of 3-bromo-1,2-carbonyldioxycyclohexene (yield 10.2%).

Appearance: colorless amorphous solid.
Melting point: 140° C. (decomp.).
IR (KBr): 1830 cm$^{-1}$ (cyclic carbonate), 1780 cm$^{-1}$ ($\beta$-lactam), 1750 cm$^{-1}$ (ester), 1690 cm$^{-1}$ (amide).

The resulting Ampicillin ester hydrochloride was incubated in 40% mouse blood in pH 7.4 phosphate buffer at 37° C. for 10 minutes, and then subjected to bioautography. It was found to be completely converted to Ampicillin.

EXAMPLE 4

(1) Production of 4-bromomethyl-1,3-dioxolen-2-one

In 200 ml of carbon tetrachloride was dissolved 8.6 g of 4-methyl-1,3-dioxolen-2-one (synthesized by the method described in U.S. Pat. No. 3,020,290). N-bromosuccinimide (17.8 g) and a catalytic amount of $\alpha,\alpha'$-azobisisobutyronitrile were added to the solution, and the mixture was heated under reflux for 90 minutes. The reaction mixture was worked up in the same way as in Example 2 to give 5.2 g (yield 33.6%) of a colorless liquid having a boiling point of 94° C./3 mm. The product had the following properties.

Elemental analysis, molecular formula $C_4H_3BrO_3$: Calculated (%): C, 26.84; H, 1.69; Br, 44.65; Found (%): C, 26.94; H, 1.66; Br, 44.60.
IR (neat): 1830 cm$^{-1}$ ($\nu_{c=o}$).
NMR (CCl$_4$, $\delta$(ppm)): 4.10 (—CH$_2$Br, s), 7.00 (=CH—O—, s).

From these data, the product was identified as the title compound.

(2) Production of Ampicillin (2-oxo-1,3-dioxolen-4-yl)methyl ester hydrochloride Ampicillin trihydrate (2 g) was dispersed in 24 ml of dimethyl formamide, and 500 mg of potassium hydrogen carbonate was added. The mixture was cooled to 0° C., and 1 ml of benzaldehyde was added. The mixture was stirred at 0° to 5° C. for 3 hours. To the mixture were added 500 mg of potassium hydrogen carbonate and 1 g of 4-bromomethyl-1,3-dioxolen-2-one, and the mixture was stirred at 0° to 5° C. for 6 hours.

After the reaction, the reaction mixture was poured into ice water, and extracted with ethyl acetate.

The extract was washed with ice water, and the ethyl acetate layer was concentrated under reduced pressure to remove ethyl acetate. The resulting syrup was dissolved in 10 ml of acetonitrile. The solution was adjusted to pH 2.0 with dilute hydrochloric acid, and stirred at 0° C. for 20 minutes.

Water (20 ml) was added, and the mixture was concentrated under reduced pressure to remove acetonitrile. The aqueous layer was repeatedly washed with ethyl acetate, and saturated with sodium chloride to precipitate an orange gum-like substance. The aqueous layer was removed by decantation. The gum-like substance was dissolved in methanol, decolorized with activated carbon, cooled to 0° C., and poured into vigorously stirred ether to precipitate a pale orange solid. The solid was collected by filtration, and washed with a mixture of ether and methanol to give 600 mg (yield 26%) of Ampicillin (2-oxo-1,3-dioxolen-4-yl)methyl ester hydrochloride as a pale orange amorphous solid.

Melting point: 130° C. (decomp.).

IR (KBr): 1835 cm$^{-1}$ (cyclic carbonate), 1790 cm$^{-1}$ ($\beta$-lactam), 1750 cm$^{-1}$ (ester), 1690 cm$^{-1}$ (amide).

NMR (D$_2$O, $\delta$(ppm)): 1.36 (6H, methyl at the 2-position, s) 4.58 (1H, proton at the 3-position, s), 5.11

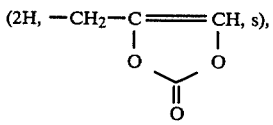
(2H, —CH$_2$—C═CH, s), 5.23 (1H, benzyl proton, s), 5.49 (1H, proton at the 5-position, d, J=2.0 Hz), 5.58 (1H, proton at the 6-position, d, J=2.0 Hz), 7.5

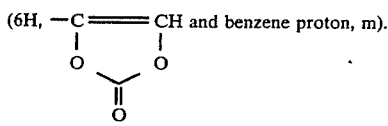
(6H, —C═CH and benzene proton, m).

The resulting Ampicillin ester hydrochloride was incubated in 40% mouse blood in pH 7.4 phosphate buffer at 37° C. for 10 minutes, and then subjected to bioautography. It was found to be completely converted to Ampicillin.

EXAMPLE 5

(1) Production of Benzylpenicillin (5-methyl-2-oxo-1,3-dioxolen-4-yl)methyl ester Ten grams of benzylpenicillin potassium salt was dispersed in 50 ml of dimethyl formamide, and with ice cooling, 520 mg of potassium hydrogen carbonate and 5.2 g of 4-bromomethyl-5-methyl-1,3-dioxolen-2-one were added, then the mixture was stirred at 0° C. for 4 hours. The reaction mixture was poured into ice water, and the precipitated solid was collected by filtration. It was dissolved in ethyl acetate, washed with a dilute aqueous solution of sodium hydrogen carbonate and then repeatedly with ice water. The ethyl acetate layer was then dried over anhydrous magnesium sulfate, and the solvent was distilled off under reduced pressure. There was obtained 12.5 g (yield 94%) of benzylpenicillin (5-methyl-2-oxo-1,3-dioxolen-4-yl)methyl ester as a pale yellow amorphous solid.

IR (KBr): 1825 cm$^{-1}$ (cyclic carbonate), 1785 cm$^{-1}$ ($\beta$-lactam), 1750 cm$^{-1}$ (ester), 1670 cm$^{-1}$ (amide)

NMR (CDCl$_3$, $\delta$(ppm)): 1.37 and 1.42 (6H, methyl at the 2-position, s), 2.13

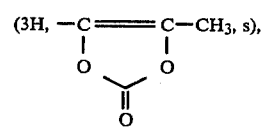
(3H, —C═C—CH$_3$, s), 3.72 (2H, —CH$_2$—C$_6$H$_5$, s) 4.29 (1H, proton at the 3-position, s), 4.80

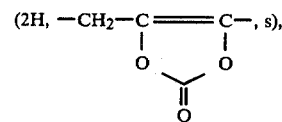
(2H, —CH$_2$—C═C—, s), 5.3–5.6 (2H, protons at the 5- and 6-positions, m), 6.16 (1H, NH, d), 7.14 (5H, protons on the benzene ring, s).

(2) Production of (5-methyl-2-oxo-1,3-dioxolen-4-yl)methyl 6-aminopenicillanate hydrochloride Phosphorus pentachloride (5.9 g) was dissolved in dry methylene chloride (30 ml), and 6.3 ml of quinoline was added. The solution was cooled to −30° C. with dry ice acetone. With vigorous stirring, 11 g of the above benzylpenicillin (2-oxo-5-methyl-1,3-dioxolen-4-yl)methyl ester dissolved in dry methylene chloride (10 ml) was added dropwise, and the mixture was stirred at this temperature for 35 minutes. Propyl alcohol (20 ml) was added dropwise over 5 minutes, and the mixture was stirred for 30 minutes. With vigorous stirring, 20 ml of a saturated solution of sodium chloride was added dropwise and the mixture was stirred for about an hour. Then, the methylene chloride layer was separated, washed with saturated sodium chloride solution, dried over anhydrous sodium sulfate and evaporated to dryness to afford a gum. The gum was washed with n-hexane and then with ethyl acetate to give 6.6 g (yield 72%) of (5-methyl-2-oxo-1,3-dioxolen-4-yl)methyl 6-aminopenicillanate hydrochloride as a pale yellow amorphous substance.

Melting point: 115°–120° C. (decomp.).

Elemental analysis, molecular formula C$_{13}$H$_{16}$N$_2$O$_6$S.HCl.$\frac{1}{2}$H$_2$O: Calculated (%): C, 41.77; H, 4.85; N, 7.49; Found (%): C, 41.91; H, 4.77; N, 7.67.

IR (KBr): 1825 cm$^{-1}$ (cyclic carbonate), 1790 cm$^{-1}$ ($\beta$-lactam), 1750 cm$^{-1}$ (ester).

NMR(DMSO-d$_6$, $\delta$(ppm)): 1.45 and 1.66 (6H, methyl at the 2-position, s) 2.22

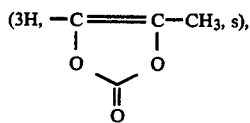

(3H, —C══C—CH₃, s), 4.57 (1H, proton at the 3-position, s), 5.0–5.2

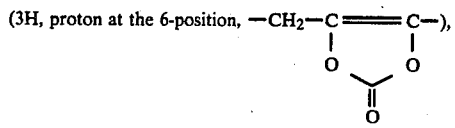

(3H, proton at the 6-position, —CH₂—C══C—), 5.56 (1H, proton at the 5-position, d).

(3) Production of D-(−)-phenylglycyl chloride hydrochloride

Separately, 10 g of D-(−)-phenylglycine was added to 250 ml of methylene chloride. The mixture was cooled to 0° C., and by passing hydrogen chloride gas, the hydrochloride of the phenylglycine was formed. Phosphorus pentachloride (20 g) was added, and the mixture was stirred at 0° to 5° C. for 4 hours. The solid precipitated was collected by filtration, and repeatedly washed with methylene chloride to give 13.1 g (yield 90%) of D-(−)-phenylglycyl chloride hydrochloride was a colorless amorphous solid.

(4) Production of Ampicillin (5-methyl-2-oxo-1,3-dioxolen-4-yl)methyl ester hydrochloride Two-hundred milligrams of the 6-aminopenicillanic acid ester hydrochloride obtained as above was dispersed in 10 ml of methylene chloride, and 50 mg of potassium hydrogen carbonate was added. The mixture was stirred at 0° C. for 15 minutes. Then, 110 mg of the acid chloride obtained as above was added, and the mixture was stirred for 2 hours and then for another 2 hours at room temperature.

After the reaction, the solid was separated by filtration, and the filtrate was concentrated under reduced pressure. The resulting syrup was dissolved in water, and washed with ethyl acetate. The aqueous layer was saturated with sodium chloride, and the separated oily substance was extracted with methylene chloride. The extract was washed with a saturated aqueous solution of sodium chloride and concentrated until the amount of methylene chloride decreased to half. Upon addition of isopropyl alcohol, a colorless solid was precipitated. The solid was collected by filtration and washed with isopropyl alcohol and ether to give 132 mg (yield 54%) of Ampicillin (5-methyl-2-oxo-1,3-dioxolen-4-yl)methyl ester hydrochloride as an amorphous solid.

The melting point and spectroscopic data of this product were identical with those of the product obtained in Example 2 (2).

EXAMPLE 6

Production of Ampicillin (2-oxo-5-phenyl-1,3-dioxolen-4-yl)methyl ester hydrochloride By the same method as shown in Example 5, (2-oxo-5-phenyl-1,3-dioxolen-4-yl)methyl 6-aminopenicillanate hydrochloride was obtained in a yield of 74% from 4-bromomethyl-5-phenyl-1,3-dioxolen-2-one and benzylpenicillin potassium salt.

Melting point: 105°–110° C. (decomp.).

Elemental analysis, molecular formula $C_{18}H_{18}N_2O_6S \cdot HCl \cdot \frac{1}{2}H_2O$: Calculated (%): C, 49.60; H, 4.62; N, 6.42; Found (%): C, 49.58; H, 4.56; N, 6.65.

IR (KBr): 1830 cm⁻¹ (cyclic carbonate), 1790 cm⁻¹ (β-lactam), 1755 cm⁻¹ (ester).

NMR(DMSO-d₆, δ(ppm)): 1.46 and 1.63 (6H, methyl at the 2-position, s), 4.55 (1H, proton at the 3-position, s), 4.95 (1H, proton at the 6-position, d), 5.36

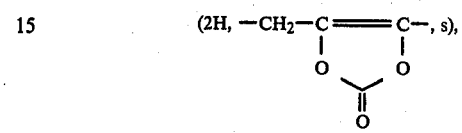

(2H, —CH₂—C══C—, s), 5.53 (1H, proton at the 5-position, s), 7.45–7.75 (5H, aromatic protons).

From 200 mg of the resulting ester hydrochloride and 95 mg of D-(−)-phenylglycyl chloride hydrochloride, 148 mg (yield 56%) of Ampicillin (2-oxo-5-phenyl-1,3-dioxolen-4-yl)methyl ester hydrochloride was obtained as a colorless amorphous solid.

The melting point and spectroscopic data of this product were identical with those of the product obtained in Example 1 (2).

EXAMPLE 7

(1) Production of (5-methyl-2-oxo-1,3-dioxolen-4-yl)methyl 6-aminopenicillanate p-toluenesulfonate In 100 ml of dimethyl formamide was dissolved 13 g of 6β-tritylaminopenicillanic acid synthesized by the method described in *Journal of American Chemical Society* 84, 2983 (1963). The solution was cooled to 0° to 5° C., and 3 g of potassium hydrogen carbonate and 6 g of 4-bromomethyl-5-methyl-1,3-dioxolen-2-one were added. The mixture was stirred at the above temperature for 3 hours. After the reaction, the reaction mixture was poured into ice water. The precipitated yellow solid was extracted with 300 ml of ethyl acetate. The ethyl acetate layer was washed several times with a saturated aqueous solution of sodium chloride, dried over anhydrous magnesium sulfate and concentrated under reduced pressure to give a yellow syrup. The syrup was dissolved in 80 ml of ethyl acetate, and with ice cooling, 5.2 g of p-toluenesulfonic acid was added. The mixture was stirred under ice cooling for 1 hour, whereupon a colorless solid precipitated. The solid was collected by filtration and well washed with ethyl acetate to give 8.3 g (yield 60%) of the title compound.

Melting point: 130°–138° C. (decomp.).

Elemental analysis, molecular formula $C_{13}H_{16}N_2O_6S \cdot CH_3C_6H_4SO_3H$: Calculated (%): C, 47.99; H, 4.83; N, 5.60 Found (%): C, 47.31; H, 4.82; N, 6.00.

IR (KBr): 1820 cm⁻¹ (cyclic carbonate), 1780 cm⁻¹ (β-lactam), 1760 cm⁻¹ (ester).

NMR (DMSO-d₆, δ(ppm)): 1.40 and 1.59 (6H, methyl at the 2-position, s), 2.12

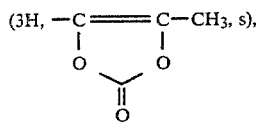

4.46 (1H, proton at the 3-position, s), 4.90–5.10

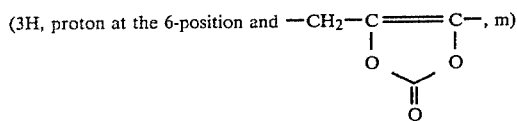

5.41 (1H, proton at the 5-position, d), 2.24

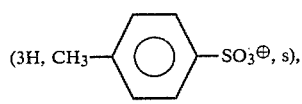

6.97 and 7.48

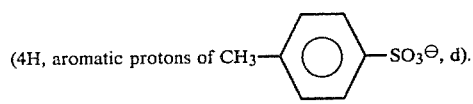

(2) Production of Ampicillin (5-methyl-2-oxo-1,3-dioxolen-4-yl)methyl ester hydrochloride Five grams of (5-methyl-2-oxo-1,3-dioxolen-4-yl)methyl 6-aminopenicillanate p-toluenesulfonate was suspended in 300 ml of ethyl acetate. To the suspension was added at 0° C. 200 ml of a 2% aqueous solution of sodium hydrogen carbonate cooled with ice. The mixture was vigorously stirred. The ethyl acetate layer was separated, washed with ice water, dried at 0° C. over anhydrous magnesium sulfate, and concentrated under reduced pressure to give a pale yellow syrup. The syrup was dissolved in 50 ml of methylene chloride. The solution was cooled to 0° C., and 1 g of potassium hydrogen carbonate and 2.1 g of D-(—)-phenylglycyl chloride hydrochloride were added, and the mixture was stirred at 0° C. for 4 hours. After the reaction, the insoluble material was separated by filtration, and the filtrate was concentrated under reduced pressure. The resulting syrup was dissolved in water and washed with ethyl acetate. The aqueous layer was saturated with sodium chloride. The separated oily substance was extracted with methylene chloride, washed with a saturated aqueous solution of sodium chloride and dried over anhydrous sodium sulfate. The dried solution was concentrated under reduced pressure until the amount of methylene chloride decreased to one half. Isopropyl alcohol was added, and the mixture was again concentrated under reduced pressure to give a colorless solid. The solid was collected by filtration, and washed with ether to give 2.6 g (yield 51%) of Ampicillin (5-methyl-2-oxo-1,3-dioxolen-4-yl)methyl ester hydrochloride as a colorless amorphous solid.

The melting point and spectroscopic data of this product were identical with those of the product obtained in Example 2 (2).

EXAMPLE 8

Formulation of an antibacterial agent:

| (1) Ampicillin (5-methyl-2-oxo-1,3-dioxolen-4-yl)methyl ester hydrochloride | 356.7 mg |
|---|---|
| Lactose | 38.3 mg |
| Magnesium stearate | 5.0 mg |
| | 400 mg in total |

The above ingredients were mixed and encapsulated to form a capsule.

| (2) Ampicillin (5-methyl-2-oxo-1,3-dioxolen-4-yl)methyl ester hydrochloride | 356.7 mg |
|---|---|
| Lactose | 613.3 mg |
| Hydroxypropyl cellulose | 30.0 mg |
| | 1,000 mg in total |

An ethanol solution of the hydroxypropyl cellulose was prepared and added to the Ampicillin ester hydrochloride and lactose. They were kneaded, extruded through a screen, and dried to form granules.

| (3) Ampicillin (5-methyl-2-oxo-1,3-dioxolen-4-yl)methyl ester hydrochloride | 356.7 mg |
|---|---|
| Crystalline cellulose | 100 mg |
| Lactose | 28.3 mg |
| Hydroxypropyl cellulose | 10 mg |
| Magnesium stearate | 5 mg |
| | 500 mg in total |

The Ampicillin ester hydrochloride, crystalline cellulose and lactose were mixed, and an ethanol solution of hydroxypropyl cellulose was added. They were kneaded and dried. To the dried mixture was added magnesium stearate. They were mixed and tabulated to form a tablet.

What is claimed is:

1. An Ampicillin ester of the formula

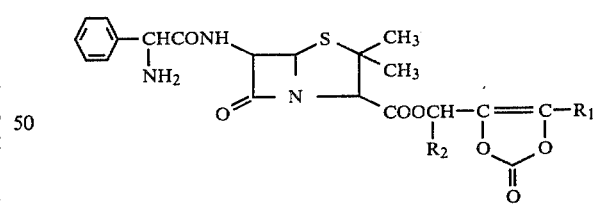

wherein $R_1$ represents a hydrogen atom, a methyl group or an aryl group, and $R_2$ represents a hydrogen atom or may be taken together with $R_1$ to form a divalent carbon chain residue, or a pharmaceutically acceptable acid addition salt thereof.

2. The compound of claim 1 wherein $R_1$ is a methyl group and $R_2$ is a hydrogen atom.

3. The compound of claim 1 wherein $R_1$ and $R_2$ are hydrogen atoms.

4. The compound of claim 1 wherein $R_1$ is a phenyl group and $R_2$ is a hydrogen atom.

5. The compound of claim 1 wherein $R_1$ and $R_2$ together form the group $-(CH_2)_3-$ or the group $-(CH_2)_5-$.

6. An antibacterial agent comprising an antibacterially effective amount of an Ampicillin ester of the formula

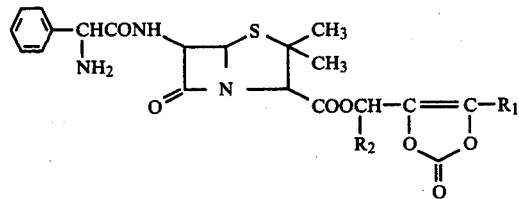

wherein $R_1$ represents a hydrogen atom, a methyl group or an aryl group, and $R_2$ represents a hydrogen atom or may be taken together with $R_1$ to form a divalent carbon chain residue, or a pharmaceutically acceptable acid addition salt thereof in association with a pharmaceutically acceptable carrier.

7. The antibacterial agent of claim 6 which is in a unit dosage form for oral administration.

8. A 6-aminopenicillanic acid ester of the formula

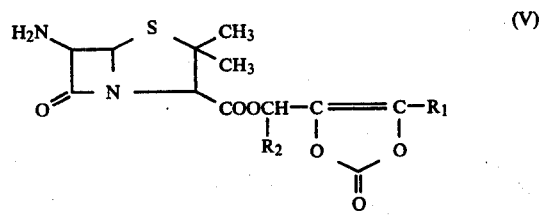

wherein $R_1$ represents a hydrogen atom, a methyl group or an aryl group, and $R_2$ represents a hydrogen atom or may be taken together with $R_1$ to form a divalent carbon chain residue, or a pharmaceutically acceptable acid addition salt thereof.

9. A process for the treatment of bacterial infectious disease which comprises administering orally to a patient in need thereof an Ampicillin ester of the formula

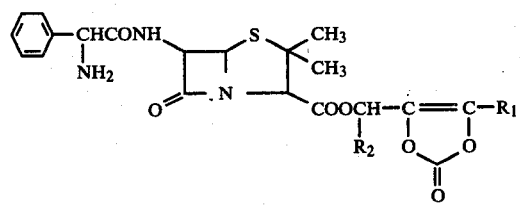

wherein $R_1$ represents a hydrogen atom, a methyl group or an aryl group, and $R_2$ represents a hydrogen atom or may be taken together with $R_1$ to form a divalent carbon chain residue, or a pharmaceutically acceptable acid addition salt thereof.

* * * * *

UNITED STATES PATENT AND TRADEMARK OFFICE
CERTIFICATE OF CORRECTION

PATENT NO. : 4,389,408

DATED : June 21, 1983

INVENTOR(S) : FUMIO SAKAMOTO; SHOJI IKEDA; GORO TSUKAMOTO and ISAMU UTSUMI

It is certified that error appears in the above-identified patent and that said Letters Patent are hereby corrected as shown below:

Column 7, last line, delete "B".

Column 12, lines 25 to 30, change the formula to read as follows:

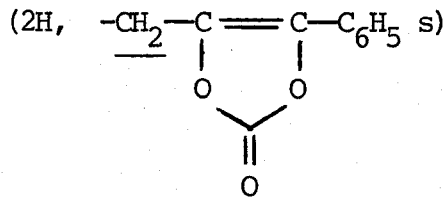

Column 13, lines 50 to 55, change the formula to read as follows:

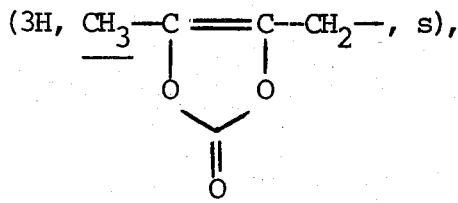

UNITED STATES PATENT AND TRADEMARK OFFICE
CERTIFICATE OF CORRECTION

PATENT NO. : 4,389,408

DATED : June 21, 1983

INVENTOR(S) : FUMIO SAKAMOTO; SHOJI IKEDA; GORO TSUKAMOTO and ISAMU UTSUMI

It is certified that error appears in the above-identified patent and that said Letters Patent are hereby corrected as shown below:

Column 7, last line, delete "B".

Column 12, lines 25 to 30, change the formula to read as follows:

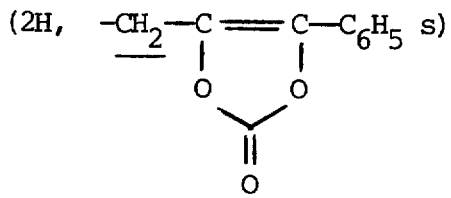

Column 13, lines 50 to 55, change the formula to read as follows:

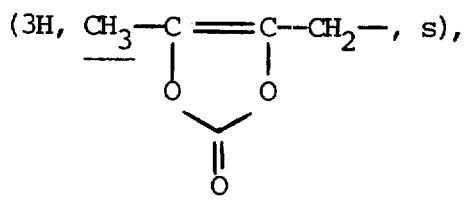

UNITED STATES PATENT AND TRADEMARK OFFICE
CERTIFICATE OF CORRECTION

PATENT NO. : 4,389,408

DATED : June 21, 1983

INVENTOR(S) : FUMIO SAKAMOTO; SHOJI IKEDA; GORO TSUKAMOTO and ISAMU UTSUMI

It is certified that error appears in the above-identified patent and that said Letters Patent are hereby corrected as shown below:

Column 13, lines 60 to 65, change the formula to read as follows:

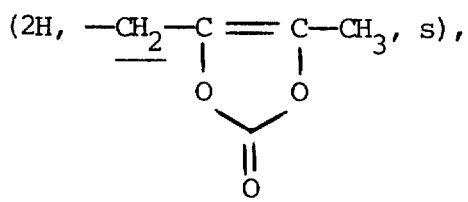

Column 15, lines 40 to 44, change the formula to read as follows:

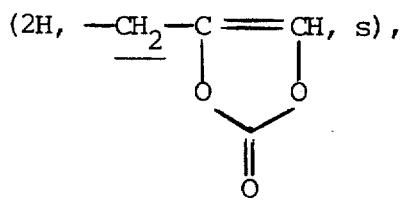

Column 17, line 30, change "was" to --as--.

UNITED STATES PATENT AND TRADEMARK OFFICE
CERTIFICATE OF CORRECTION

PATENT NO. : 4,389,408

DATED : June 21, 1983

INVENTOR(S) : FUMIO SAKAMOTO; SHOJI IKEDA; GORO TSUKAMOTO and ISAMU UTSUMI

It is certified that error appears in the above-identified patent and that said Letters Patent are hereby corrected as shown below:

Column 19, lines 17 to 23, change the formula to read as follows:

Signed and Sealed this

Tenth Day of January 1984

[SEAL]

Attest:

GERALD J. MOSSINGHOFF

Attesting Officer

Commissioner of Patents and Trademarks